United States Patent
Timmins

(10) Patent No.: US 7,888,001 B2
(45) Date of Patent: Feb. 15, 2011

(54) SYSTEM AND METHODS FOR MEASURING A SKIN PROTECTION FACTOR

(75) Inventor: Graham S. Timmins, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 30 days.

(21) Appl. No.: 11/827,034

(22) Filed: Jul. 10, 2007

(65) Prior Publication Data

US 2008/0056995 A1 Mar. 6, 2008

Related U.S. Application Data

(60) Provisional application No. 60/819,843, filed on Jul. 11, 2006.

(51) Int. Cl.
*A61K 49/00* (2006.01)
*G01N 24/10* (2006.01)
*C12M 1/34* (2006.01)
*C12Q 1/02* (2006.01)

(52) U.S. Cl. .................. 435/4; 424/9.2; 435/288.7; 435/29; 514/460

(58) Field of Classification Search .................. None
See application file for complete search history.

(56) References Cited

U.S. PATENT DOCUMENTS

2005/0288573 A1* 12/2005 Timmins .................... 600/410

FOREIGN PATENT DOCUMENTS

| WO | WO 2004/039414 | * 5/2004 |
|---|---|---|
| WO | WO2004039414 | 5/2004 |
| WO | WO2005117698 | 12/2005 |

OTHER PUBLICATIONS

Collins et al. (1995) Photochem.Photobiol. 62(3): 557-560.*
Jurkiewicz et al. (1995) J. Invest. Dermatol. 104(4): 484-488.*
Budai et al. (2004) 77: 27-38.*
Jurkovic (2003) Eur. J. Pharma. Biopharma. 56: 59-66.*
Sanchez et al. (2002) Eur. J. Biochem. 269: 6133-6141.*
Collins et al, EPR Persistence Measurements of UV-Induced Melanin Free Radicals in Whole Skin. Photochem. Photobiol. Jun. 1995, vol. 62, No. 3, pp. 557-560, especially pp. 557-558.
Jurkiewicz et al, Effect of Topically Applied Tocopherol on Ultraviolet Radiation-Mediated Free Radical Damage in Skin. J. Invest. Dermatology. Apr. 1995, vol. 104, No. 4, pp. 484-488, especially pp. 485-487.

* cited by examiner

*Primary Examiner*—Lisa J Hobbs
(74) *Attorney, Agent, or Firm*—Valauskas Corder LLC

(57) ABSTRACT

The present invention is a system and methods of establishing a Melanocyte Protection Factor (MPF), which indicates the level of protection against DNA damage to a target cell, such as the level of protection a particular sunscreen offers against UVA rays when compared to the unprotected case, i.e., no sunscreen. The present invention determines and records levels of stable melanin radicals (SMR) in a target cell. Light is applied to the target cell forming light-induced melanin radicals (LIR). The levels of SMR and intensity of LIR are measured to determine the amount of incident light reaching the target cell. Since LIR is proportional to the square root of light intensity reaching the target cell, the ratio of light reaching the target cell is defined as the MPF:

$$MPF = \frac{UV \text{ reaching melanocyte without sunscreen}}{UV \text{ reaching melanocyte with sunscreen}} = \frac{\left[\frac{SMR_{+screen}}{LIR_{+UV+screen}}\right]^2}{\left[\frac{SMR_{control}}{LIR_{+UV\ control}}\right]^2}.$$

6 Claims, 9 Drawing Sheets

No Sunscreen

LIR + SMR +UV Control

Sunscreen Applied

LIR +SMR +UV +Screen

SYSTEM AND METHODS FOR MEASURING A SKIN PROTECTION FACTOR

This application claims the benefit of U.S. Provisional Application No. 60/819,843 filed Jul. 11, 2006.

FIELD OF THE INVENTION

The present invention relates generally to measuring a skin protection factor, and more particularly to measuring ultraviolet A rays radiation (UVA) to determine a Melanocyte Protection Factor (MPF).

BACKGROUND OF THE INVENTION

The sun emits ultraviolet (UV) radiation in the form of A rays (UVA), B rays (UVB), and C rays (UVC). The approximate wavelength band, or range, in nanometers for UVA is 400-320 nm, UVB is 320-280 nm, and UVC is below 280 nm. Due to absorption in the atmosphere's ozone layer, 99% of the ultraviolet radiation that reaches the Earth's surface is UVA. The total UVA and longer wavelengths of light at the Earth surface vastly exceeds that of UVB, with this differential increasing with increasing latitude, decreasing altitude, increasing daytime from solar noon, and temporal distance from summer solstice.

The Sun Protection Factor (SPF) is a laboratory measure of the effectiveness of sunscreen: the higher the SPF, the more protection a sunscreen offers against UVB (the ultraviolet radiation that causes sunburn).

SPF represents an endpoint indicative of sensitivity to UVB. The SPF endpoint indicates the time a person can be exposed to sunlight before developing a condition commonly known as "sunburn" with a sunscreen applied relative to the time they can be exposed without sunscreen. For example, someone who would develop the sunburn condition—or also more commonly "burn"—after 12 minutes in the sun would expect to burn after 2 hours (120 min) if protected by a sunscreen with SPF 10. In practice, the protection from a particular sunscreen depends on a variety of factors including skin type, amount and frequency of sunscreen applied, and amount of sunscreen the skin absorbs, to name a few. Sunscreen is commonly considered to be a lotion applied topically and promoted as a way of reducing sunburn.

SPF is typically measured by applying sunscreen to the skin of a volunteer and measuring how long it takes the volunteer to develop a sunburn when exposed to an artificial sunlight source. This is considered an "in vivo", measurement of the efficacy of a sunscreen. SPF can also be measured "ex vivo", that is, through experimentation in a controlled environment outside a living organism. Ex vivo measurements of SPF are typically performed with the help of a specially designed spectrometer, that is, a device used to measure properties of light. In this case, the actual transmittance of the sunscreen is measured, along with the degradation of the product due to being exposed to sunlight. The transmittance of the sunscreen must be measured over all wavelengths in the UVB band (290-350 nm), along with a table of how effective various wavelengths are in causing sunburn (the erythema action spectrum) and the actual intensity spectrum of sunlight, or solar irradiance spectrum. Such ex vivo measurements agree very well with in vivo measurements.

Mathematically, the SPF is calculated from measured data as $$SPF = \frac{\int A(\lambda)E(\lambda)d\lambda}{\int A(\lambda)E(\lambda)/mPF(\lambda)d\lambda}$$

where; $E(\lambda)$ is the solar irradiance spectrum; $A(\lambda)$ is the erythema action spectrum; and $mPF(\lambda)$ is the monochromatic protection factor; and all functions of the wavelength $\lambda$. The mPF is roughly the inverse of the transmittance at a given wavelength $\lambda$, or the ratio of the ultraviolet intensities recorded at wavelength $\lambda$ before and after application of a sun protecting product. More simplistically, SPF is time or dose of UVB rays to cause minimal erythema on protected skin divided by time or dose of UVB rays to cause minimal erythema on unprotected skin. Erythema is an abnormal redness of the skin caused by solar radiation, commonly termed sunburn.

SPF is an imperfect measure of skin damage because invisible damage and skin aging is also caused by the very common UVA, which does not cause reddening or pain. SPF does not measure the UVA protection of sunscreens. Conventional sunscreens do not block UVA as effectively as UVB. UVA also causes deoxyribonucleic acid (DNA) damage to certain cells deep within the skin, known as melanocytes, thereby increasing the risk of photoaging, including wrinkles or discoloration, and melanoma. Melanoma is a malignant tumor of melanocytes. Melanocytes are cells located in the bottom layer of the epidermis, or outermost layer of the skin. Although melanoma is one of the rarer types of skin cancer, it causes the majority of skin cancer related deaths.

Melanoma rates have been increasing over the years. Annual percent increases were of 2.5% between 1992 and 2001. Melanoma has disproportionately high mortality in younger age groups, such as 18 to 40 year olds, with each death resulting in a loss of almost 19 years of expected life, among the highest for adult onset cancers. Although it remains unclear how ultraviolet light causes melanoma, it is suggested that melanoma is caused by oxidative stress damage to DNA in the melanocytes caused by longer wavelengths, such as UVA.

Difficulties remain in measuring real-life UVA protection of sunscreens. Current methods to measure UVA protection include Persistent Pigment Darkening (PPD) and Immediate Pigment Darkening (IPD). PPD is the persistent darkening of the skin observed after UVA exposure whereas IPD is the transitory darkening of the skin observed after UVA exposure. Although these methods measure UVA protection, these methods are not accurate, reliable or reproducible. These methods fail to determine important parameters such as photostability of the skin with sunscreen, absorption and permeation of sunscreen, and water-resistance of the sunscreen.

Persistent Pigment Darkening (PPD) measures UVA protection by comparing results from sunscreen protected skin and unprotected skin to determine UVA-protection factors (UVA-PF). PPD's clinical significance is said to be questionable because the spectrum for PPD is not defined for wavelengths shorter than 320 nm. PPD requires high doses of UVA, which in some instances is unrealistic. In addition, the results are masked during outdoor sun exposure by other skin responses to ultraviolet radiation. Thus, it is impossible to relate the PPD protection factor directly to the degree of UVA protection to sunlight.

Immediate Pigment Darkening (IPD) concerns immediate reactions induced by UVA radiation on the skin surface. IPD is thought not to be a precise method since it is difficult to detect for all skin phototypes. Skin phototype is determined by the amount of melanin pigment in the skin. Skin phototype is based on a scale from one (pale white skin) to six (dark brown or black skin). Problems with IPD include that it does not show up on pale or fair phototypes and it is difficult to detect on dark phototypes. The IPD that develops after exposure to UVA rays does not allow for a precise measurement of UVA protection to sunlight.

There is a demand for a measure of a skin protection factor of UVA rays that is accurate, reliable, and can be used as a world-wide standard. The present invention satisfies this demand.

SUMMARY OF THE INVENTION

The present invention measures a skin protection factor of UVA rays, otherwise referred to herein as a Melanocyte Protection Factor (MPF), or UVA endpoint. MPF represents an endpoint indicative of sensitivity to UVA, such that it indicates the level of protection against DNA damage to melanocytes. DNA damage includes photoaging, such as wrinkles or discoloration, and melanoma. The MPF conveys the damage caused by light as well as the efficacy of products, such as sunscreen or clothing. Light, in the broad sense, is the total spectrum of electromagnetic radiation. The spectrum of electromagnetic radiation comprises gamma rays, x-rays, ultraviolet, visible spectrum, infrared, terahertz radiation, microwave, radio waves; listed from shortest to longest wavelength. For purposes of this application light is ultraviolet (UV) light or visible light (such as blue light). Light includes artificial light such as a light bulb or natural light such as sunlight. Light can also be direct and indirect.

UVA rays cause DNA damage to target cells, known as melanocytes, located in the bottom layer of the epidermis, or outermost layer of the skin. Melanocytes produce melanin, which is the primary determinant of human skin phototype, or color. Thus, melanocytes are also referred to herein as melanin-containing cells. Melanin is the central photosensitizing chromophore, or part of a molecule that reacts upon receiving wavelengths of light. Melanin is responsible for melanoma causation and reacts upon exposure to light that ranges from UVB to UVA to visible light.

UVA is likely a major causative factor in human melanoma, and sunscreens are a widely used form of sun protection, yet until the present invention, it is has been difficult to assess and identify UVA protection abilities to a level that is as well understood as the SPF measurement of UVB protection. For purposes of this application, sunscreen is anything that an individual can use in the effort to help protect the skin from ultraviolet radiation, and includes, for example, a medical treatment, topical product, such as a lotion or spray, or article of clothing. Sunscreen includes commercial and non-commercial products.

FIG. 1 graphically illustrates the penetrance of light through 100 microns of epidermis. A depth of 100 microns is chosen because this is typically where the target cells, or melanocytes, reside. As shown, short wavelength UVB (280-320 nm) is absorbed directly by DNA, but penetrates shallowly into the skin, while UVA is poorly absorbed by DNA, but penetrates deeper into the skin. The graphical illustration of FIG. 1 has been verified in human skin nevus where deeper cells harbor proportionately more UVA-caused mutations than skin mutations resultant from UVB exposure. The term "nevus" is generally known to refer to a concentration of melanocytes. Nevus includes pigmented skin, such as isolated lesions or simply dark or heavily pigmented skin. Nevi are usually benign. For example, nevi include most birthmarks and moles. The term nevus includes melanocytic nevus, for example focal melanocytic hyperplasia (FMH), blue nevus, and possibly dysplastic nevus.

The present invention is a system and methods of establishing a Melanocyte Protection Factor (MPF), which indicates the level of protection offered, for example, by a sunscreen, against UVA rays causing DNA damage to melanocytes. The level of protection can be compared to the unprotected case, i.e., no sunscreen. The present invention seeks to determine levels of stable melanin radicals (SMR) in a target cell. Ultraviolet light is directed to the target cell forming light-induced melanin radicals (LIR), otherwise referred to herein as light-induced radical (LIR) and reactive melanin radicals (RMR). The levels of SMR and intensity of LIR are measured to determine the amount of incident light, or rays of light that strike the target cell. LIR is proportional to the square root of light intensity reaching the target cell, thus, the ratio of light reaching the target cell is defined as the MPF:

$$MPF = \frac{UV \text{ reaching melanocyte without sunscreen}}{UV \text{ reaching melanocyte with sunscreen}} = \frac{\left[\frac{SMR_{+screen}}{LIR_{+UV+screen}}\right]^2}{\left[\frac{SMR_{control}}{LIR_{+UV\ control}}\right]^2}$$

The MPF index of protection to the target cell includes establishing a decrease in transmission of the ultraviolet light and calculating a reciprocal of ultraviolet light transmission. For purposes of this application, transmittance refers to the mathematical quantity of light passing through the target cell, where as transmission refers to the physical process.

The present invention utilizes Electron Paramagnetic Resonance (EPR) approaches to measure LIR, either in vivo or ex vivo. The present invention measures UVA protection utilizing various bands of the light spectrum, including a full solar simulated spectrum, filtered UVA spectrum, or isolated waveband, which amounts to a range of wavelengths. Any spectrum band can be used to measure UVA protection because of wavelength dependence on the production of melanin.

The present invention includes a system to establish the MPF. A device, such as a computer, determines and records a first baseline level of stable melanin radicals (SMR) in a nevus. A light source is used that emits light having sufficient intensity to irradiate melanin in the nevus and form light-induced melanin radicals (LIR), while the device measures a first level of SMR and a first intensity of LIR. Irradiate is the common term to identify the process by which an item is exposed to radiation, here ultraviolet light. A sunscreen, such as a topical product or an article of clothing, is applied to the nevus such that the computer determines and records a second baseline level of SMR as well as a second level of SMR and a second intensity of LIR. A computational device, such as the computer described above, calculates a ratio of the intensity of the light reaching the nevus without sunscreen and with sunscreen.

An object of the present invention is to reduce melanoma incidence.

Another object of the present invention is to determine the damage caused by exposure to light, specifically UVA rays. Light includes artificial light and natural light and further includes direct and indirect exposure.

An additional object of the present invention is to determine sunscreen efficacy, or the effectiveness that a topical product or clothing offers against UVA rays.

Yet another object of the present invention is to correlate UVA protection measurements with prevention of an outcome, such as melanoma or photoaging.

An added object of the present invention is to provide an easily interpreted measure of UVA protection. An easily interpreted measure of UVA protection may inform consumers of the protection offered by certain sunscreens and allows them to comparison shop. Ultraviolet protective clothing is becoming more prevalent, and the UVA protection measurement according to the present invention allows consumers to choose between different sunscreens, or to assess likely effectiveness of multiple sunscreens.

Another object of the present invention is to determine UVA protection by the measurement of a relevant biologicial endpoint. SPF represents an endpoint indicative of sensitivity to UVB. The SPF endpoint indicates the time a person can be exposed to sunlight before getting sunburn with a sunscreen applied relative to the time they can be exposed without sunscreen. According to the present invention, MPF represents an endpoint indicative of sensitivity to UVA. The UVA endpoint indicates the level of protection a particular sunscreen offers against UVA rays causing damage to melanocytes, when compared to the unprotected case.

A further object of the present invention is to provide a measure of UVA protection that is applicable to all living organisms, including humans. The method of the present invention measures parameters that can be fully evaluated in living skin, such as photostability of the skin with sunscreen, absorption and permeation of sunscreen, and water-resistance of the sunscreen. Since humans are subject to complex patterns of ultraviolet exposure, effects of ultraviolet radiation can be performed in animal models, and then correlated to humans.

Yet another object of the present invention is to provide a measure of UVA protection that is objective and not dependent upon interpretation by an observer.

An additional object of the present invention is to measure UVA protection using filtered UVA light, full spectrum solar simulated light, or isolated wavebands of light.

An added object of the present invention is to measure UVA protection at any intensity of UVA rays.

Another object of the present invention is to provide UVA protection measurements that are compatible with SPF.

Another object of the present invention is to eliminate loss of resolution at higher MPF protection factors. For example, a difference between protection of SPF 5 and SPF 10 is easily determined whereas a difference between protection of SPF 25 and SPF 30 is not easily determined, even though the numerical difference between the two cases is the same. The present invention eliminates the loss of resolution between differing MPFs.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The patent or application contains at least one drawing executed in color. Copies of this patent or application with color drawings will be provided by the Patent Office upon request and payment of the necessary fee.

DETAILED DESCRIPTION OF EMBODIMENTS OF THE INVENTION

The *Xiphophorus* freshwater fish model is a well established model for assessing human malignant melanoma. The stages of melanoma progression which have been characterized from melanomas in humans are similar to those found in *Xiphophorus* fish. To date, the *Xiphophorus* model is the only known model in which the action spectrum for melanoma is known. The action spectrum illustrates wavelength dependence of a phenomenon, such as melanoma or photoaging.

The present invention includes an action spectrum of light-induced melanin radical (LIR), also referred to herein as light-induced radical (LIR) and reactive melanin radicals (RMR), formation in the skin. The illumination of melanin by ultraviolet and blue light generates stable melanin radicals (SMR) and LIR.

The present invention utilizes Electron Paramagnetic Resonance (EPR) to measure LIR in skin, and generate an action spectrum of LIR in the skin. The action spectrum of LIR formation in the skin was compared to the known action spectrum of the *Xiphophorus* model and proved to be identical. Thus, melanin photosensitized production of free radicals is the central event in melanoma causation. Measurement of LIR correlates to the incidence of melanoma.

Figure 1:
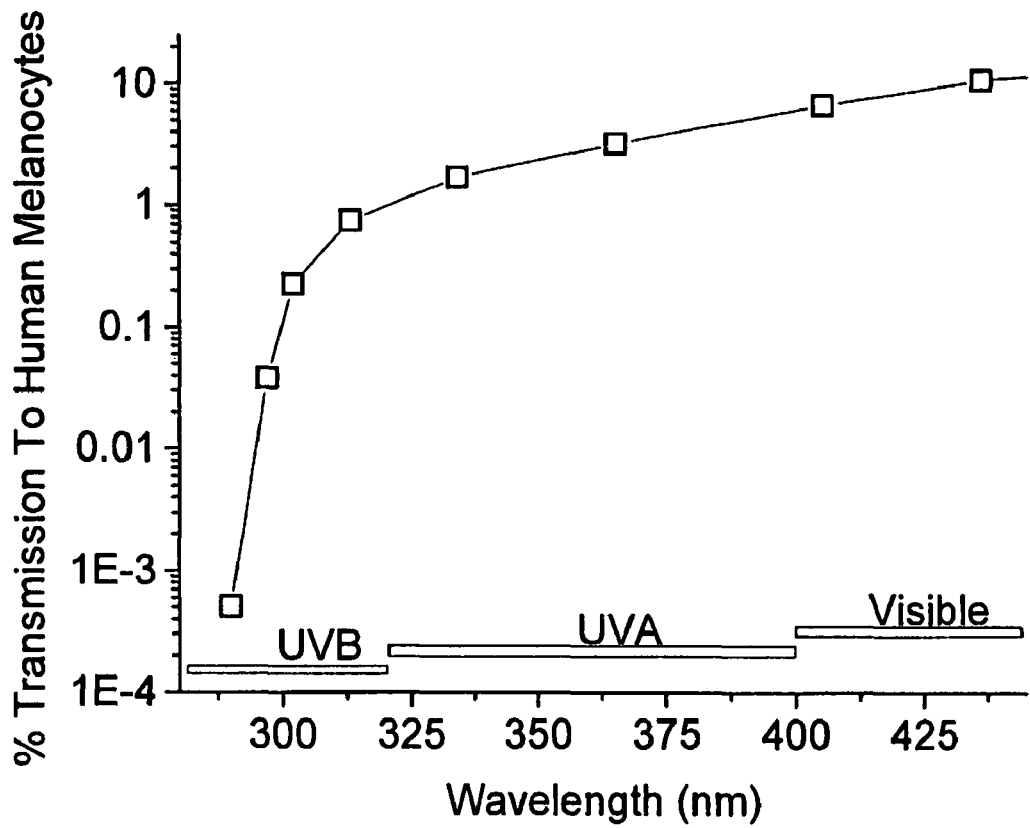
FIG. 1 graphically illustrates the penetrance of various wavelengths of light through skin according to the present invention.
Figure 2:
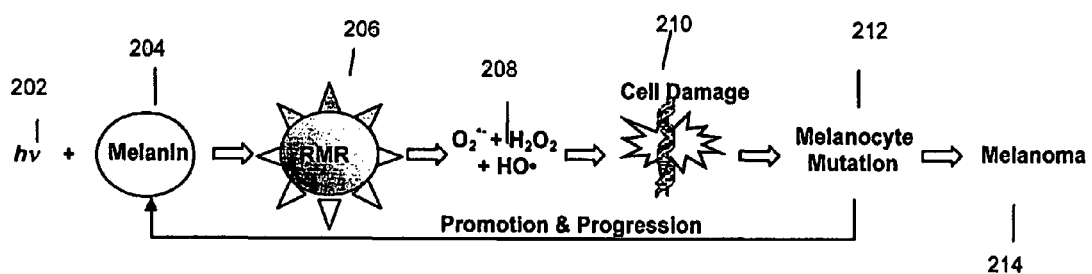
FIG. 2 diagrammatically represents the role of light-induced melanin radicals (LIR) in the causation of melanoma according to the present invention.

FIG. 2 diagrammatically represents the role of LIR in the causation of melanoma. Ultraviolet light transmits to the target cells, or melanocytes, at 202. As shown by 204, the melanocyte includes melanin. The melanin in the melanocyte absorbs the ultraviolet light generating LIR (or RMR) at 206. At 208, the LIR produces small molecular weights of oxidants, such as superoxide ($O_2^-$) hydrogen peroxide ($H_2O_2$), and hydroxyl radical (HO), to name a few. Damage to the DNA in the melanocyte results at 210 causing mutations in the melanocyte at 212. The mutations accumulate and lead to melanoma as shown at 214.

Figure 3:
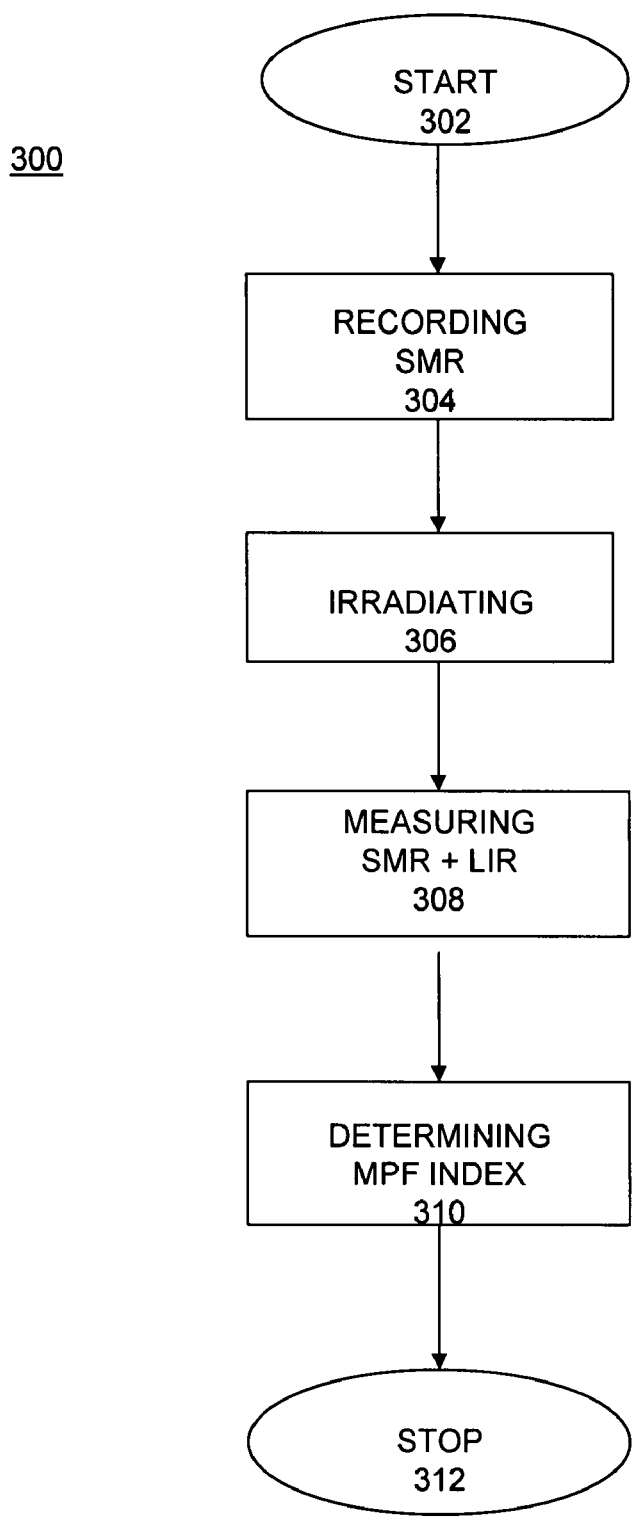
FIG. 3 is a method of the Melanocyte Protection Factor (MPF) according to the present invention.

FIG. 3 is a method 300 of the Melanocyte Protection Factor (MPF) according to the present invention. MPF indicates the level of protection against DNA damage to melanocytes, such as the level of protection a particular sunscreen offers against UVA rays when compared to no sunscreen.

The method 300 has a first step 302 in which a nevus is provided from which levels of stable melanin radicals (SMR) are determined and recorded at step 304. At step 306, light is applied to the nevus forming light-induced melanin radicals (LIR). At step 308, the levels of SMR and intensity of LIR are measured to determine the amount of incident light reaching the concentration of melanocytes of the nevus. The MPF index is determined at 310. Since LIR is proportional to the square root of light intensity reaching the melanocytes of the nevus, the ratio of light reaching the melanocyte is defined as:

$$MPF = \frac{UV \text{ reaching melanocyte without sunscreen}}{UV \text{ reaching melanocyte with sunscreen}} = \frac{\left[\frac{SMR_{+screen}}{LIR_{+UV+screen}}\right]^2}{\left[\frac{SMR_{control}}{LIR_{+UV\ control}}\right]^2}$$

Figure 4:
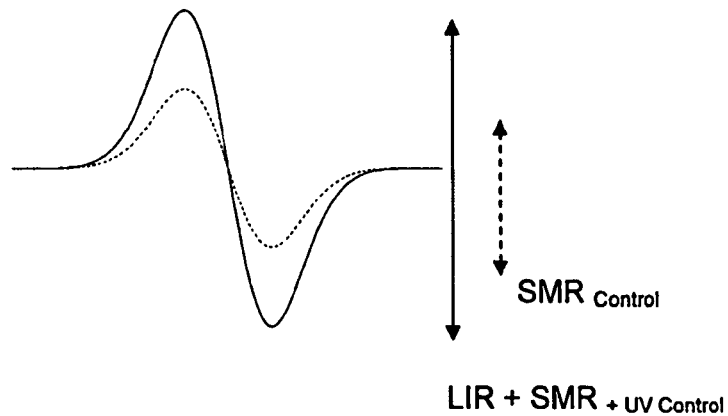
FIG. 4 graphically illustrates the sensitivity of melanoma and non-melanoma skin cancer at different wavelengths according to the present invention.
Figure 4:
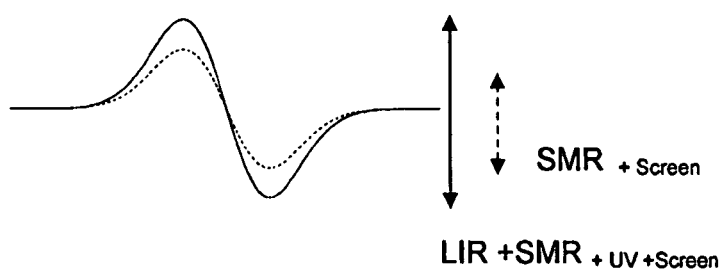

FIG. 4 graphically illustrates the sensitivity of melanoma and non-melanoma skin cancer at different wavelengths. To determine the sensitivity of the LIR measurement at different wavelengths, the action spectrum of LIR formation (from the *Xiphophorus* model) and the International Commission on Illumination (CIE) action spectrum for erythema are convoluted with typical solar emission spectra. Thus, the relative sensitivities of LIR and erythema to UVA and UVB of sunlight, or full spectrum solar simulated light are determined.

As shown in FIG. 4, the data results are normalized for the integrated area under the curve. It can be seen that erythema is overwhelmingly caused by UVB, with over 80% of erythema caused by these wavelength and less than 20% by UVA. Thus, a sunscreen that blocked 99.9% of all UVA wavelengths but not UVB, would have virtually no detectable SPF, as total removal of UVA would only result in an SPF of 1.25. In contrast, it can be seen that over 95% of measured LIR (or SMR) would be caused by UVA, with less that 5% by UVB, thus a sunscreen that blocked 99.9% of UVB, but not UVA, would offer virtually no protection against LIR formation, and so would have no MPF. This waveband selectivity leads to the possibility of using full-spectrum solar simulated light and obtaining discrete measurements of UVB and UVA protection by simply measuring the appropriate endpoint—SPF for UVB and MPF for UVA. Use of full spectrum solar simulated light overcomes many of the disadvantages of measurement techniques that can only use filtered wavelength ranges. Furthermore, the relative ratio of SPF to MPF gives a direct measure of the relative performance of UVA and UVB protection: an SPF much higher than the MPF would indicate low UVA protection, while equal SPF and MPF would indicate similar effectiveness in blocking UVA and UVB.

Figure 5:
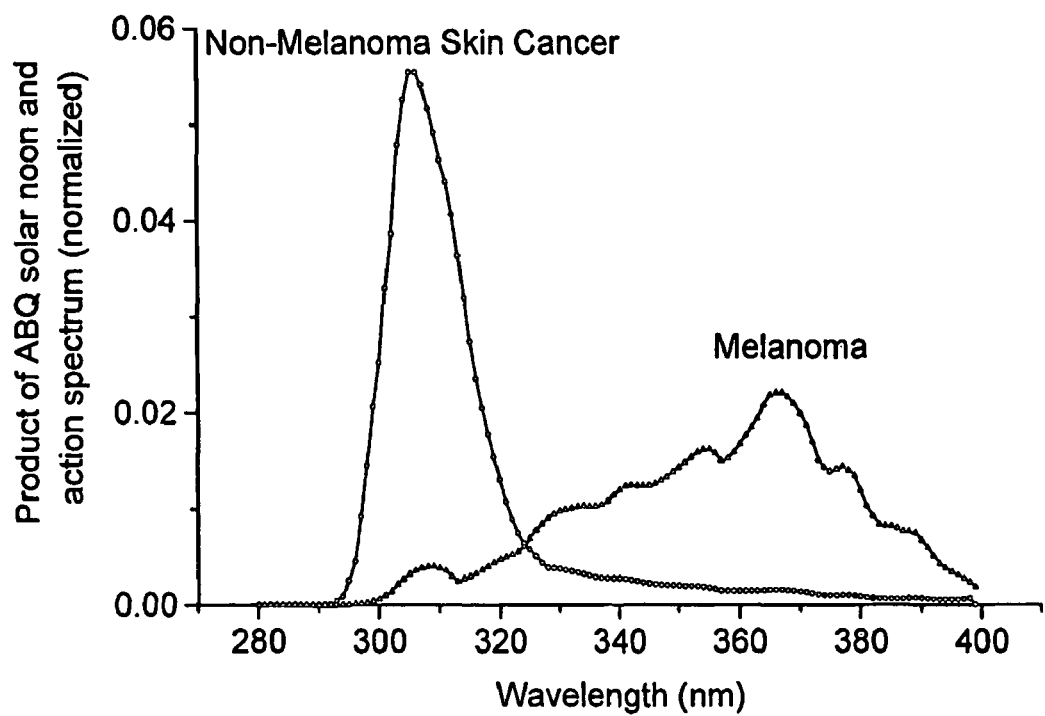
FIG. 5 diagrammatically represents Electron Paramagnetic Resonance (EPR) measurement of light-induced melanin radicals (LIR) and stable melanin radicals (SMR) in normal and sunscreen treated melanocytes according to the present invention.

As previously detailed, melanin also contains SMR, so that an accurate measurement of LIR can be achieved by measuring the levels of SMR before light irradiation of the sample, and measuring LIR and SMR during irradiation with a light source. This is diagrammatically shown in FIG. 5.

Based upon the above, the screening effect of sunscreens as a function of wavelength in melanin was analyzed.

First, defined composition sunscreens in the form of topical lotions were produced. These sunscreens contained either 6% oxybenzone or 3% avobenzone as active filters. These concentrations represent the Food and Drug Administration (FDA) allowable maximums for these agents. Sunscreens were made by adding 3% avobenzone or 6% oxybenzone to 4% stearic acid, 0.5% cetyl alcohol, 1% silicone 200 fluid (food grade, 350 cs), 4% Ganex V-220, 2% Amphisol and 0.1% propyl paraben with heating to 85° C. while stirring. Separately, water (balance of 100%), 5% propylene glycol, 0.1% Carbopol 940 and 0.2% methyl paraben were heated to 75° C. with stirring. The oil phase was then added to the aqueous phase with stirring and allowed to cool to 50° C. when 0.1% triethanolamine was added. The mixture was stirred continuously and allowed to cool to room temperature. All final percentages are weight for weight percentages. Sunscreen was stored in light-excluding vials until use within 6 months.

Commercial sunscreens were purchased from a local store and used within 2 years. The commercial SPF 4 sunscreen was labeled as "UVA/UVB Protection" and contained octylmethoxycinnamate and oxybenzone as active filters. The commercial SPF 30 sunscreen was labeled with terms "UVA/UVB Protection" and "With Avobenzone for extra UVA protection" and contained avobenzone, homosalate, octisalate, octocrylene and oxybenzone.

Figure 6:
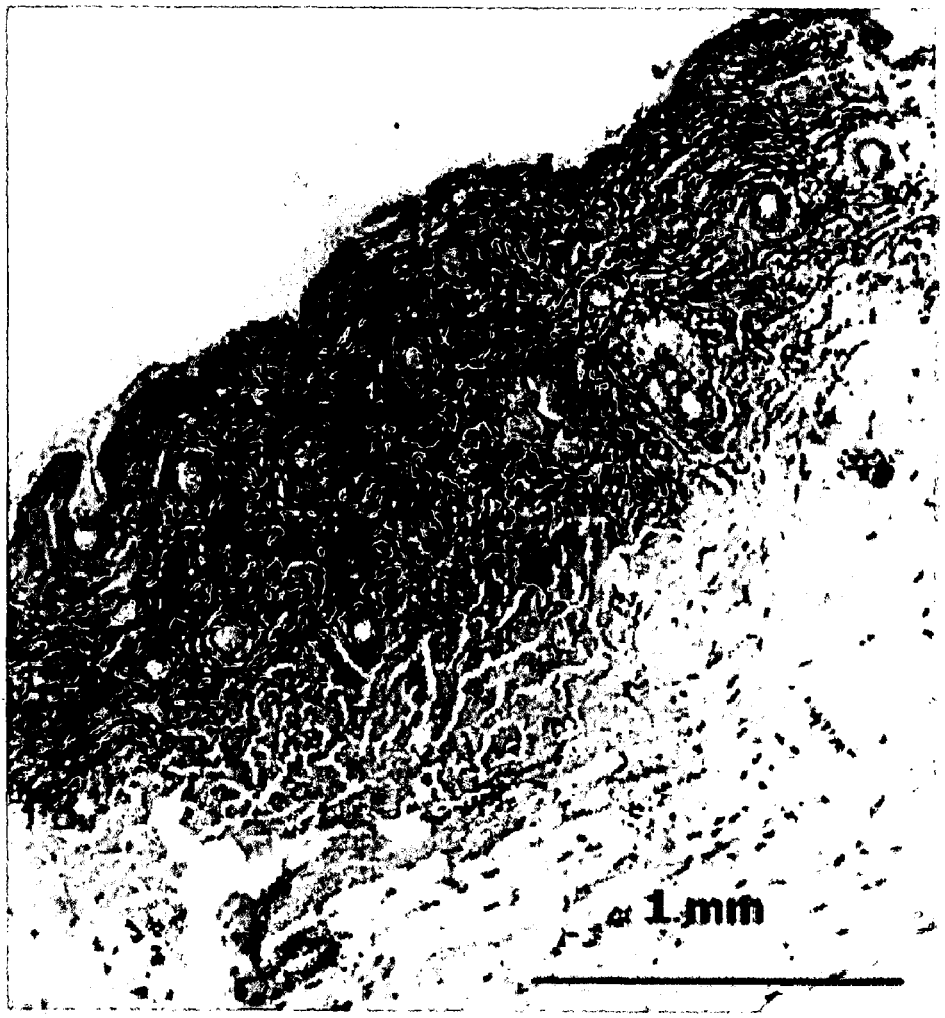
FIG. 6 illustrates a hematoxylin and eosin-stained section of a typical focal melanocytic hyperplasia (FMH) lesion according to the present invention.

Areas of Focal Melanocytic Hyperplasia (FMH) were induced by two applications of 100 μL of 0.5% dimethylbenzanthracene (DMBA) in ethanol to the shaved backs of animals. Two months after DMBA treatment, animals were killed, lesion multiplicity determined, and FMH lesions collected on ice in humidified sealed plastic containers and used within 4 hours. A hematoxylin and eosin-stained section of a typical FMH lesion (after fixation, embedding, sectioning and staining by conventional techniques) is shown in FIG. 6. A 1 $cm^2$ area of skin was excised containing an FMH lesion in the center, subcutaneous fat and tissue removed, and a 6 mm diameter sample was removed with a circular punch and used for EPR spectroscopy. Each FMH lesion was used for only one measurement. FMH lesions were uniformly pigmented to visual inspection, and were selected on the basis of a diameter greater than 3 mm to ensure high signal-to-noise ratios in the EPR spectra.

Figure 7:
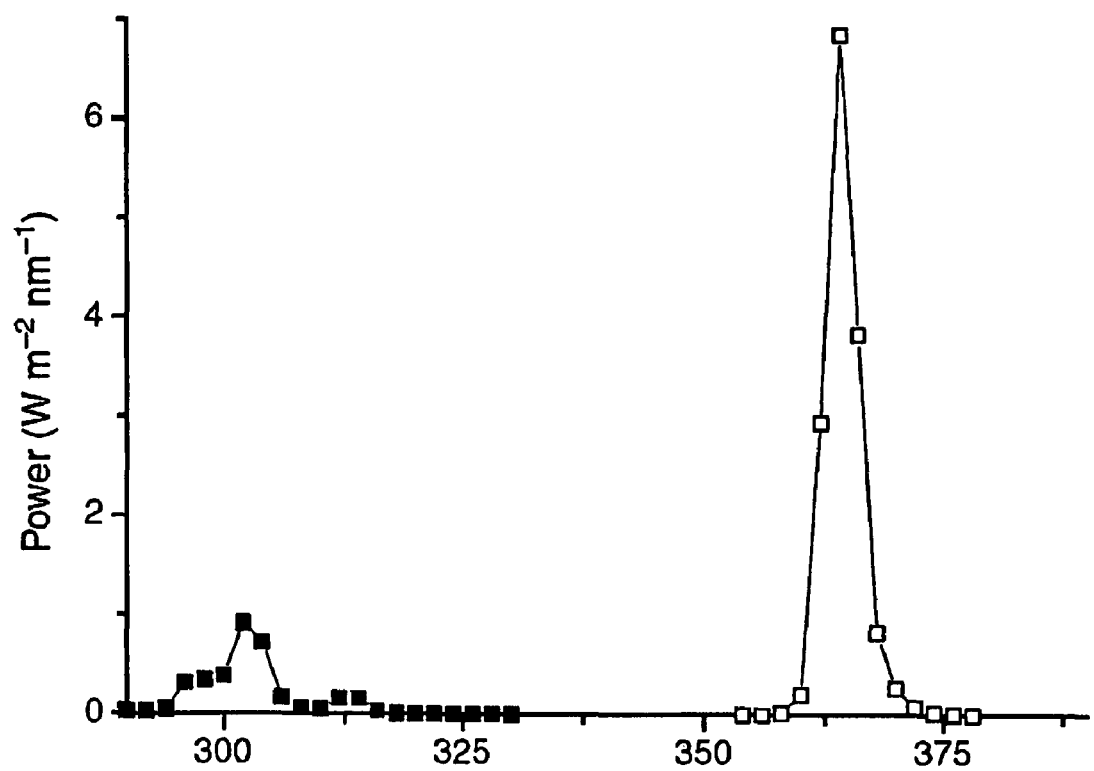
FIG. 7 graphically illustrates spectral emission profiles according to the present invention.

Ultraviolet light from a 500 W XeHg arc lamp was filtered with a dichroic mirror and water filter to remove infrared wavelengths, i.e., filtered UVA light. Specific mercury (Hg) line wavebands were isolated using UV interference filters and were also filtered with a WG320 filter to remove UVB except when 302 nm and 313 nm radiation was used. A liquid light guide provided filtered light to the EPR cavity. The emission profile for each filter combination with the light guide assembly was determined using a calibrated Optronics model 742 scanning spectroradiometer. Typical output spectra are shown for the 302 nm and 365 nm wavebands are shown in FIG. 7, with integrated powers of 7.0 and 30.1 W $m^{-2}$, respectively. These were compared to UVB and UVA powers typically measured (in Albuquerque, N. Mex. at solar noon in summer) of 1.5 and 40 W $m^{-2}$ respectively. The proportionality of the EPR signal of the light-induced radical (LIR) to the root of the incident power was verified for each wavelength used by using calibrated neutral density filters.

The FMH sample was mounted in a specially constructed polytetrafluoroethylene sample cell with a silica UV transparent window with a small water-saturated filter paper to prevent sample desiccation. The sample was placed in a High Sensitivity resonator X-band EPR cavity of a Bruker Elexsys E540 EPR spectrometer. EPR spectroscopy was performed at X-band (9 GHz) frequencies, using nonsaturating microwave powers (5 mW incident) and 100 kHz modulation. EPR spectra were recorded by sweeping the magnetic field through resonance while action spectrum experiments were performed by fixing the magnetic field at the spectral maximum of the melanin radical and recording the signal as a function of UV irradiation as previously described. After measurements of the untreated skin sample were completed in quadruplicate (sample removed and returned to account for any minor variation in EPR intensity due to differing sample orientation), sunscreen was carefully applied to the skin surface at 2 mg cm$^{-2}$, as per the FDA monograph for SPF, and gently rubbed in using a fingercot. The experiment was repeated. The decrease in transmission of UV to the melanocytes was determined and calculated as the reciprocal of transmission. All values are presented as mean ±1 standard deviation.

The EPR spectra of SMR and LIR are identical, so that LIR appear as an increase in the amplitude of the melanin radical spectrum upon irradiation. Thus, measurement of LIR can be achieved by measuring the levels of SMR before light irradiation of the sample, and (LIR+SMR) measured during irradiation with the appropriate light source. This ratio is used to derive the protection provided to the melanocytes in which this index is determined. As the low light intensities from a highly filtered lamp resulted in relatively low LIR signals in comparison with SMR, especially with sunscreen, LIR is measured by fixing the magnetic field at the spectral maximum of the melanin radical.

Figure 8:
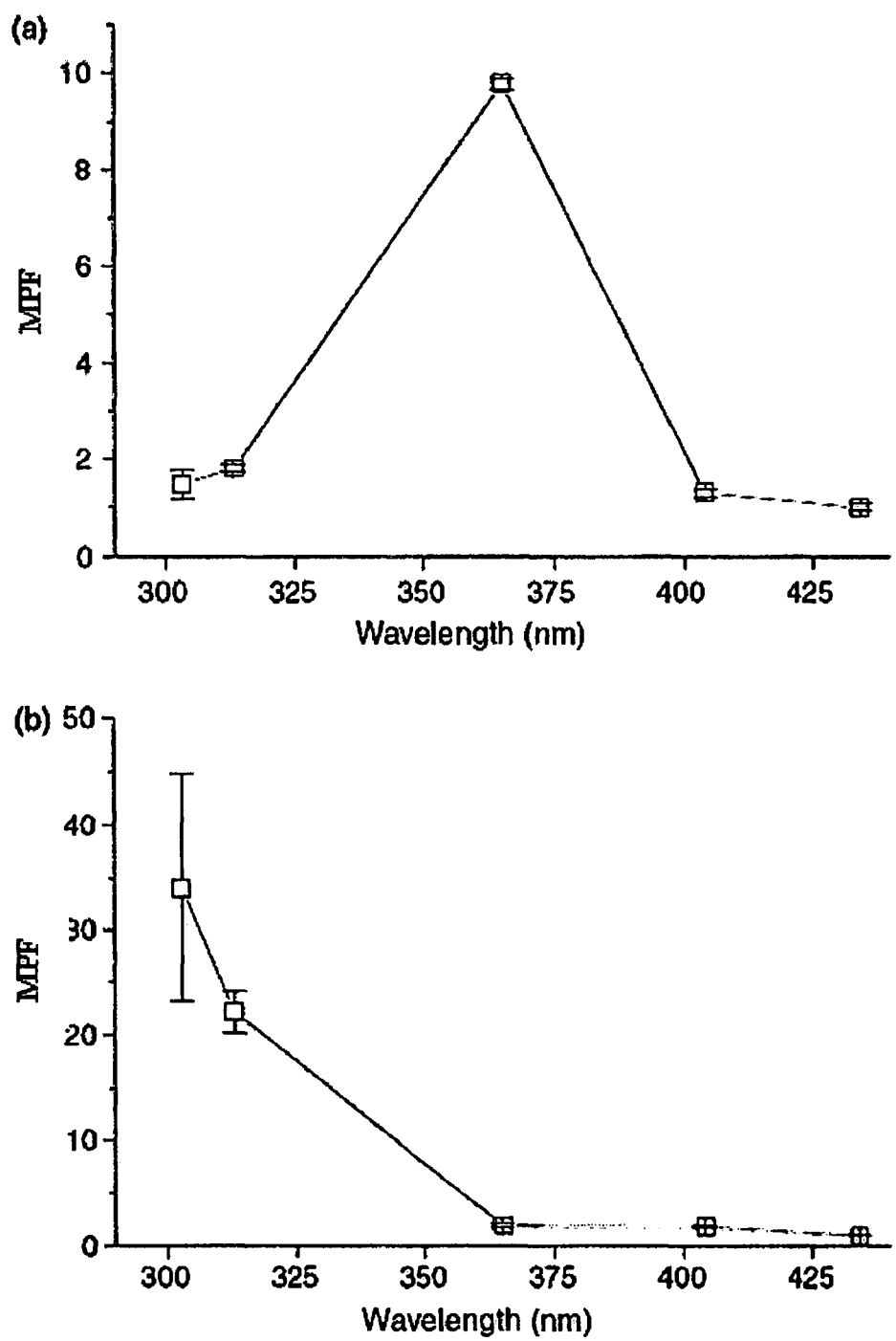
FIG. 8 graphically illustrates wavelength specific ultraviolet protection factors for non-commercial sunscreens according to the present invention.

The MPF of the four sunscreens at 302 nm, 313 nm, 365 nm, 404 nm and 434 nm, wavelengths that range from UVB to visible, were determined. No significant protection was observed for any product at 404 nm or 434 nm as may be expected from the sunscreen agents used, and the lack of inorganic particulates such as ZnO or TiO$_2$. The wavelength dependence of MPF for the two defined research formulations containing 3% avobenzone and 6% oxybenzone are shown in FIG. 8a, b, respectively. Oxybenzone offered substantial UVB protection but little protection at 365 nm and longer wavelengths. In contrast, avobenzone offered substantial protection at 365 nm (MPF=9.8±0.2), but little protection against UVB. This is in accord with their known ex vivo screening abilities. The larger standard deviations in the 303 nm point for 6% oxybenzone derive from the combination of lower emission power and high absorption at this wavelength introducing uncertainties in LIR measurement after sunscreen application.

Figure 9:
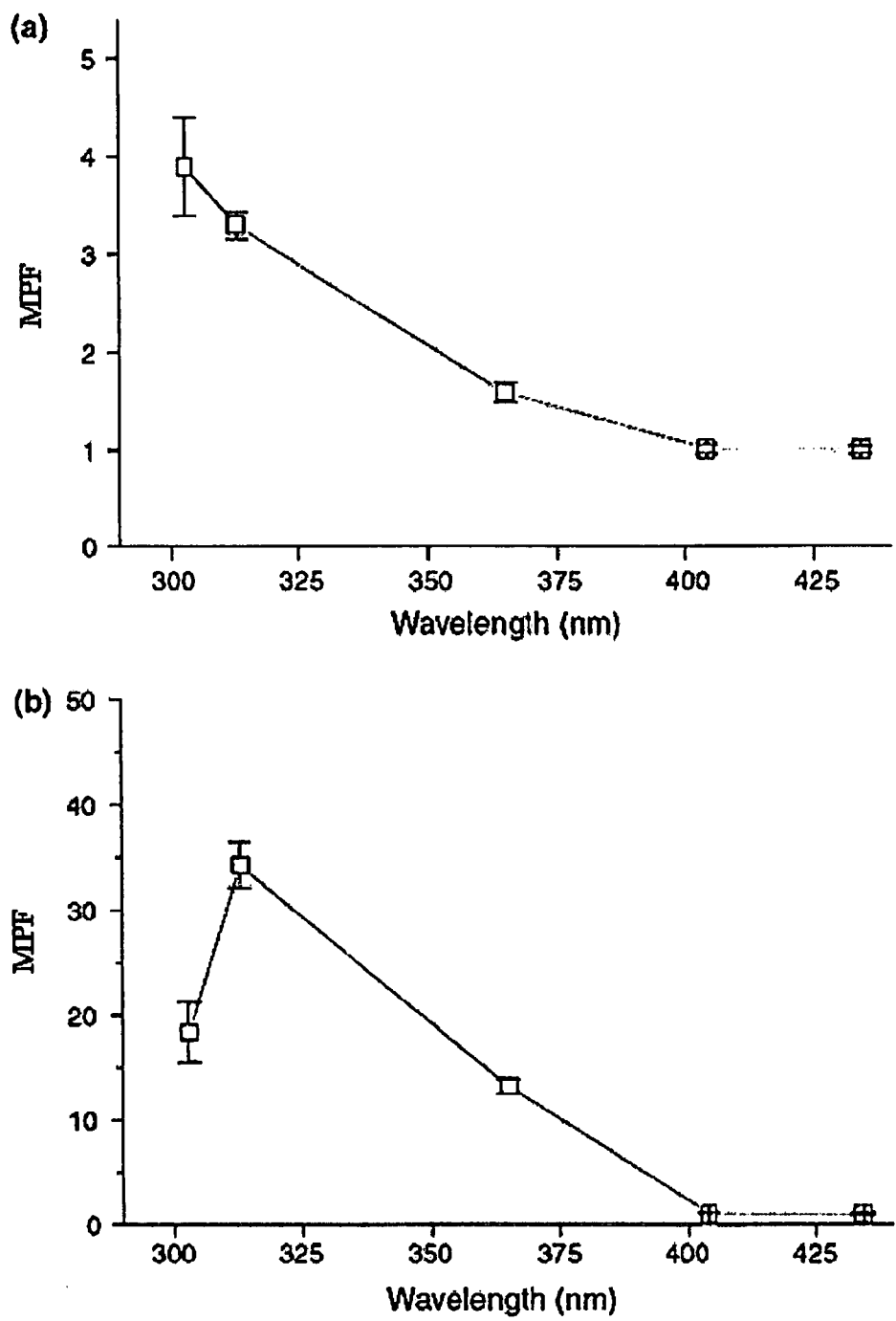
FIG. 9 graphically illustrates wavelength specific ultraviolet protection factors for commercial sunscreens according to the present invention.

The wavelength dependence of MPF for the two commercial sunscreens is shown in FIG. 9a, b, respectively. It can be seen for the SPF 4 product that the MPF at UVB wavelengths was about 4, as would be expected from the SPF rating of the product, while the MPF at 365 nm was only 1.6±0.1. Thus, although this product is identified as providing UVA/UVB protection, its ability to screen UVA wavelengths in skin is less than for UVB. For the SPF 30 product, the MPF at 303 nm and 313 nm was 18±2.8 and 34±2.1, respectively, in broad accord with its SPF 30 rating, although the MPF at 365 nm was only 13±0.8. The SPF 30 formulation contained avobenzone, an approved FDA UVA filter, yet it is clear that the protection of even this product against UVA when applied to skin is substantially less than it affords against UVB.

The present invention utilizes EPR approaches to measure LIRs in a nevus-like skin lesion from an animal model of melanoma. The induction of LIR with monochromatic wavelengths was used to determine the MPF of sunscreen products that have been applied to the nevus-like skin lesion. This approach can allow the measurement and design of UVA and UVB protection of sunscreens without having to make assumptions about the action spectrum of melanoma causation, or any other photobiological effect. The measurement is robust and measures a defined physical-chemical endpoint that does not require subjective analysis. When combined with other approaches, such as SPF, a detailed understanding of sunscreen protection can be delineated. Although isolated wavebands to characterize MPF were used, solar-simulated broadband UVB or UVA could readily be applied to generate protection factors for UVB and UVA. Furthermore, convolution of the action spectra for erythema and LIR with solar emission spectra indicates that almost all erythema (the SPF endpoint) is caused by UVB, while almost all LIR is caused by UVA. By using a full spectrum UV source alone, with the SPF and LIR endpoints, the UVB and UVA protection of sunscreens could be assessed.

As expected, oxybenzone (6%) provides substantial MPF in the UVB, about 20-30, and so can provide the basis for UVB protection in high SPF sunscreens. Avobenzone (3%) provided little MPF in the UVB, but an MPF for UVA (at 365 nm) of about 10. As this is the maximal concentration of avobenzone correctly allowed by the FDA, it may prove difficult to use this agent alone to generate sunscreens that have MPFs in the UVA range greater than about 15. Because many commercial sunscreens are of SPF 30 or greater, this the protective capacity for UVA may be much lower than for UVB. This was observed for the commercial SPF 30 sunscreen assayed which had an MPF at 365 nm of less than half the quoted SPF.

Commercial sunscreens have less UVA protection in comparison to UVB protection, which has been observed in skin using ascorbyl radical formation to determine oxidative stress damage. It is contemplated the present invention can use ascorbyl radical formation to determine MPF, although it should be noted that certain sunscreen agents can act as photooxidizing sensitizers that may complicate the determination of efficacy of the sunscreen. It is further contemplated the present invention can use low-frequency EPR, which allows such EPR measurements to be taken from skin in vivo. These will greatly facilitate application to humans, and allow complete characterization of sunscreen products such as water-resistance and photostability.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A method of establishing efficacy of sunscreen, comprising:
    (a) isolating a nevus;
    (b) recording levels of stable melanin radicals (SMR) in the nevus;
    (c) inducing melanin in the nevus to form light-induced melanin radicals (LIR);
    (d) measuring levels of SMR and intensity of LIR;
    (e) administering sunscreen to the nevus;
    (f) repeating steps (b)-(d); and
    (g) determining an index of protection relative to the nevus according to the equation:

$$MPF = \frac{UV \text{ reaching melanocyte without sunscreen}}{UV \text{ reaching melanocyte with sunscreen}} = \frac{\left(\frac{SMR_{+screen}}{LIR_{+UV+screen}}\right)^2}{\left(\frac{SMR_{control}}{LIR_{+UVcontrol}}\right)^2}.$$

2. The method of claim 1, wherein said step of measuring levels of SMR and intensity of LIR further comprises a step of using Electron Paramagnetic Resonance (EPR).

3. The method of claim 2, wherein said step of using Electron Paramagnetic Resonance (EPR) includes in vivo or ex vivo.

4. The method of claim 1, wherein said step of inducing melanin in the nevus further comprises a step of providing filtered UVA light and a step of irradiating the nevus.

5. The method of claim 1, wherein said step of inducing melanin in the nevus further comprises a step of irradiating the nevus with full spectrum solar simulated light.

6. The method of claim 1, wherein said step of inducing melanin in the nevus further comprises a step of isolating wavebands of light and a step of irradiating the nevus with the isolated wavebands of light.

* * * * *